US011730640B2

(12) United States Patent
Morimoto et al.

(10) Patent No.: US 11,730,640 B2
(45) Date of Patent: Aug. 22, 2023

(54) NONWOVEN SUBSTRATE FOR WEARABLE ARTICLES

(71) Applicant: The Procter & Gamble Company, Cincinnati, OH (US)

(72) Inventors: Koichi Morimoto, Beijing (CN); Meng Chen, Beijing (CN); Lili Sun, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 1031 days.

(21) Appl. No.: 16/550,412

(22) Filed: Aug. 26, 2019

(65) Prior Publication Data

US 2019/0374406 A1 Dec. 12, 2019

Related U.S. Application Data

(63) Continuation of application No. PCT/CN2017/074990, filed on Feb. 27, 2017, and a
(Continued)

(51) Int. Cl.
*A61F 13/514* (2006.01)
*A61F 13/49* (2006.01)
(Continued)

(52) U.S. Cl.
CPC .. *A61F 13/51456* (2013.01); *A61F 13/15699* (2013.01); *A61F 13/496* (2013.01);
(Continued)

(58) Field of Classification Search
CPC .. A61F 13/15; A61F 13/514; A61F 13/51456; A61F 13/64
See application file for complete search history.

(56) References Cited

U.S. PATENT DOCUMENTS 7,901,393 B2  3/2011  Matsuda et al.
8,298,205 B2  10/2012  Norrby et al.
(Continued)

FOREIGN PATENT DOCUMENTS

CN      1824867 A    8/2006
CN    101501892 A    8/2009
(Continued)

OTHER PUBLICATIONS

International Search Report and Written Opinion, PCT/CN2017/074993, dated Mar. 6, 2019.
(Continued)

*Primary Examiner* — Michele Kidwell
(74) *Attorney, Agent, or Firm* — Charles R. Matson; Richard L. Alexander

(57) ABSTRACT

Disclosed is a wearable article continuous in a longitudinal direction and a transverse direction comprising a body-facing surface and a garment-facing surface; wherein at least a portion of the garment-facing surface is a nonwoven substrate material made of fibers having a Roughness (standard deviation of the grayscale image) of at least about 16, preferably at least about 18, more preferably at least about 20; and a fiber diameter of no more than about 22 μm, preferably no more than about 17 μm, more preferably no more than about 15 μm, according to the measurements herein.

13 Claims, 8 Drawing Sheets

Related U.S. Application Data continuation-in-part of application No. PCT/CN2017/089994, filed on Jun. 26, 2017.

(51) Int. Cl.

| | | |
|---|---|---|
| *A61F 13/496* | (2006.01) | |
| *A61F 13/15* | (2006.01) | |
| *A61F 13/64* | (2006.01) | |
| *D04H 1/558* | (2012.01) | |
| *D04H 1/541* | (2012.01) | |

(52) U.S. Cl.
CPC ........ *A61F 13/49009* (2013.01); *A61F 13/64* (2013.01); *D04H 1/5412* (2020.05); *D04H 1/5414* (2020.05); *D04H 1/558* (2013.01); *A61F 13/15723* (2013.01); *A61F 2013/49063* (2013.01)

(56) References Cited

U.S. PATENT DOCUMENTS

| | | | |
|---|---|---|---|
| 8,622,983 B2 | 1/2014 | Wilkes et al. | |
| 9,220,643 B2 | 12/2015 | Mariko et al. | |
| 9,421,134 B2 | 8/2016 | Schlinz et al. | |
| 9,549,859 B2 | 1/2017 | Wilkes et al. | |
| 11,298,273 B2* | 4/2022 | Morimoto | A61F 13/496 |
| 2003/0124303 A1 | 7/2003 | Price | |
| 2004/0102757 A1 | 5/2004 | Olson | |
| 2004/0158214 A1* | 8/2004 | Ponomarenko | A61F 13/51121 604/385.01 |
| 2004/0243083 A1 | 12/2004 | Matsuda et al. | |
| 2006/0030831 A1 | 2/2006 | Matsuda et al. | |
| 2010/0069864 A1 | 3/2010 | Berland et al. | |
| 2011/0160692 A1 | 6/2011 | Wilkes et al. | |
| 2011/0183568 A1* | 7/2011 | Haubruge | D04H 3/147 156/244.11 |
| 2014/0088542 A1 | 3/2014 | Wilkes et al. | |
| 2014/0116945 A1* | 5/2014 | Kas | B01D 67/0004 210/651 |
| 2016/0089275 A1 | 3/2016 | Ruman et al. | |
| 2016/0331600 A1 | 11/2016 | Polidori et al. | |
| 2017/0156945 A1 | 6/2017 | Hashimoto et al. | |
| 2017/0165128 A1 | 6/2017 | Morimoto et al. | |
| 2017/0189244 A1 | 7/2017 | Mueller et al. | |
| 2017/0335498 A1 | 11/2017 | Hansen et al. | |
| 2018/0168885 A1 | 6/2018 | Zink et al. | |

FOREIGN PATENT DOCUMENTS

| | | |
|---|---|---|
| CN | 105208988 A | 12/2015 |
| CN | 106456403 A | 2/2017 |
| EP | 0820746 A1 | 1/1998 |
| EP | 3326596 | 5/2018 |
| JP | H11256464 A | 9/1999 |
| WO | 0071067 A1 | 11/2000 |
| WO | 0130289 A1 | 5/2001 |
| WO | 2016029566 A1 | 3/2016 |
| WO | 2016048337 A1 | 3/2016 |
| WO | 2016103801 A1 | 6/2016 |
| WO | WO2016168997 | 10/2016 |
| WO | 2016195631 A1 | 12/2016 |

OTHER PUBLICATIONS

International Search Report and Written Opinion; Application Ser. No. PCT/CN2017/089994, dated Dec. 1, 2017, 9 pages.

* cited by examiner

NONWOVEN SUBSTRATE FOR WEARABLE ARTICLES

CROSS REFERENCE TO RELATED APPLICATIONS

This application is a continuation, under 35 USC 120, of Application No. PCT/CN2017/074990, filed on Feb. 27, 2017 and Application No. PCT/CN2017/089994, filed on Jun. 26, 2017, both of which are herein incorporated by reference in their entirety.

FIELD OF THE INVENTION

The present invention relates to nonwoven substrates suitable for use in wearable articles.

BACKGROUND OF THE INVENTION

Infants and other incontinent individuals wear absorbent articles such as diapers to receive and contain urine and other body exudates. Absorbent articles may be the taped type which has fastening members which are fastened by the wearer or caregiver to configure the waist opening and leg openings, or the pull-on or pant-type, which are donned by inserting the wearer's legs into the pre-formed leg openings and sliding up the article into position about the lower torso.

Whatever the structure of the article may be, the outer surface, or garment-facing surface of the article may be the portion which is most touched and observed by the wearer or the caregiver upon use, and thus its properties most associated with the quality and function of the article. By quality, what may be desired is an undergarment kind of appearance, and pleasant tactile sense such as softness and cushiony touch. By function, what may be desired is a stretchable element in the form of portions of the belt or fastening member, which assures secure wearability.

Meanwhile, from a manufacturer's point of view, there is desire to provide a high quality absorbent article while controlling cost for making the article; by selecting materials and assembling them in a manner that may provide the best user experience per cost of material.

Based on the foregoing, there is a need for a wearable article having improved tactile and aesthetic sense for the garment-facing surface without compromise to the wearability performance. There is further a need for providing parameters that guide the manufacturer to select materials and to assemble them in a manner that provides a favorable return of investment for manufacturing a wearable article.

SUMMARY OF THE INVENTION

The present invention is directed to a wearable article continuous in a longitudinal direction and a transverse direction comprising a body-facing surface and a garment-facing surface; wherein at least a portion of the garment-facing surface is a nonwoven substrate material made of fibers having a Roughness (standard deviation of the grayscale image) of at least about 16, preferably at least about 18, more preferably at least about 20; and a fiber diameter of no more than about 22 µm, preferably no more than about 15 µm, according to the measurements herein.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

DEFINITIONS

Figure 1:
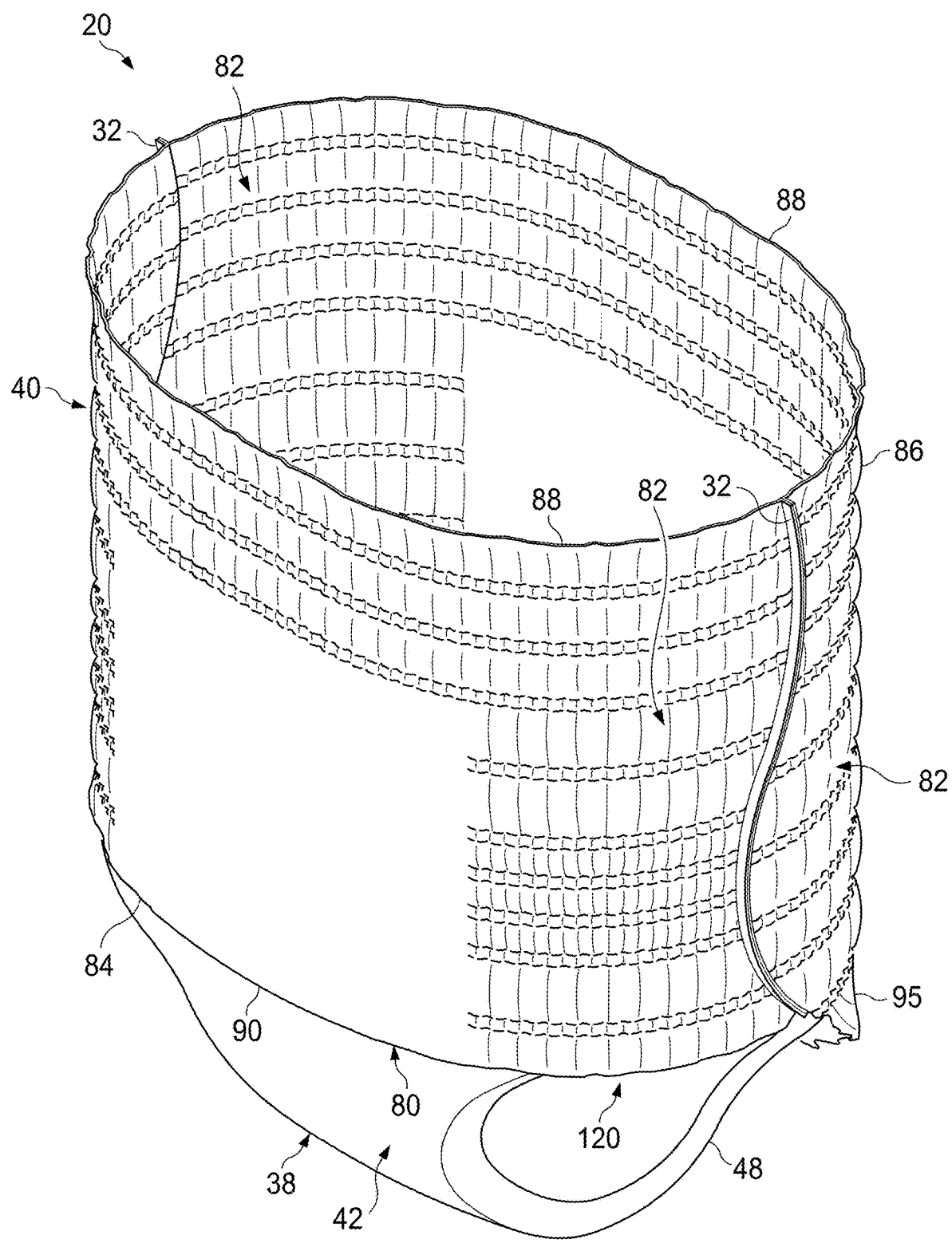
FIG. 1 is a perspective view of one embodiment of a wearable article of the present invention.

As used herein, the following terms shall have the meaning specified thereafter:

"Wearable article" refers to articles of wear which may be in the form of pants, taped diapers, incontinent briefs, feminine hygiene garments, and the like. The "wearable article" may be so configured to also absorb and contain various exudates such as urine, feces, and menses discharged from the body. The "wearable article" may serve as an outer cover adaptable to be joined with a separable disposable absorbent insert for providing absorbent and containment function, such as those disclosed in PCT publication WO 2011/087503A.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants".

"Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Proximal" and "distal" refer respectively to the position closer or farther relative to the longitudinal center of the article.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable".

"Extendibility" and "extensible" mean that the width or length of the component in a relaxed state can be extended or increased.

"Elasticated" and "elasticized" mean that a component comprises at least a portion made of elastic material.

"Elongatable material", "extensible material", or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Artwork" refers to a visual presentation to the naked eye, which is provided by printing or otherwise, and having a color. Printing includes various methods and apparatus well known to those skilled in the art such as lithographic, screen printing, flexographic, and gravure ink jet printing techniques.

"Color" or "Colored" as referred to herein includes any primary color except color white, i.e., black, red, blue, violet, orange, yellow, green, and indigo as well as any declination thereof or mixture thereof. The color white is defined as those colors having an L* value of at least 94, an a* value equal to 0±2, and a b* value equal to 0±2 according to the CIE L* a* b* color system.

DETAILED DESCRIPTION OF THE INVENTION

Figure 2:
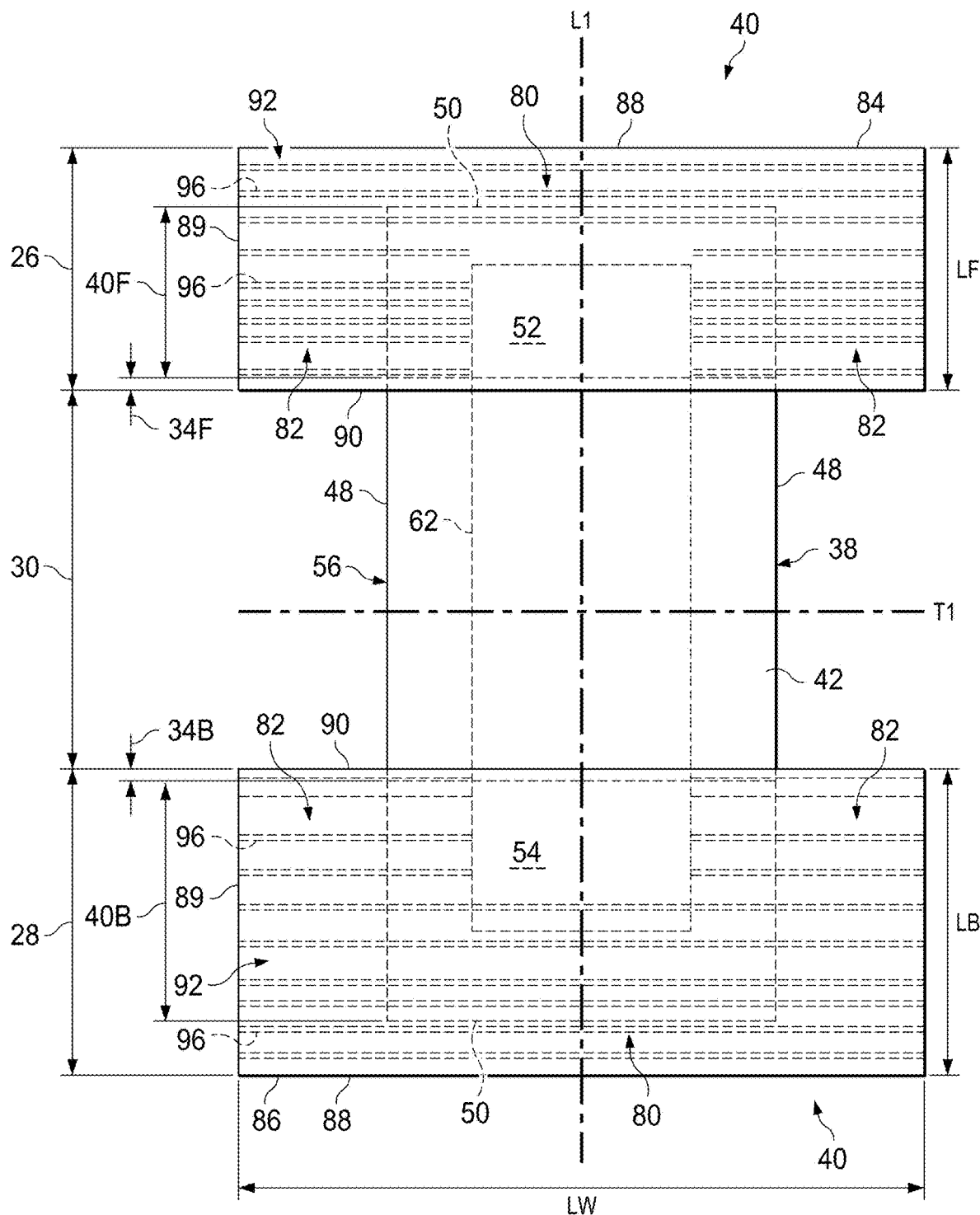
FIG. 2 is a schematic plan view of one embodiment of a wearable article of the present invention with the seams enjoined and in a flat uncontracted condition showing the garment facing surface.

FIG. 1 is a perspective view of an embodiment of the wearable article 20 of the present invention of the pant-type and FIG. 2 is a schematic plan view of the same article with the seams unjoined and in its flat uncontracted condition showing the garment-facing surface. The wearable article 20 has a longitudinal centerline L1 which also serves as the longitudinal axis, and a transverse centerline T1 which also serves as the transverse axis. The wearable article 20 has a body facing surface, a garment facing surface, a front region 26, a back region 28, a crotch region 30, and seams 32 which join the front region 26 and the back region 28 to form two leg openings and a waist opening. At least a portion of the garment-facing surface is a nonwoven substrate material made by a specific nonwoven substrate of the present invention described in detail below. The wearable article 20 may be a belt-type pant comprising a central chassis 38 to cover the crotch region of the wearer, a front belt 84 and a back belt 86 (hereinafter may be referred to as "front and back belts"), the front and back belts 84, 86 forming a discrete ring-like elastic belt 40 (hereinafter may be referred to as "waist belt") extending transversely defining the waist opening. For the belt-type pant, the discrete ring-like elastic belt 40 may also be referred to as the elastic belt region 40. For the belt-type pant, the front and back belts 84, 86 and the central chassis 38 jointly define the leg openings. The wearable article 20 may be a uni-body pant wherein the central chassis 38 is continuous with the front and back belt 84, 86, wherein the leg openings are continuously formed. For the uni-body pant, the belt portion existing between the side seams are considered the elastic belt region 40, wherein the region is considered to terminate by an imaginary line running in the transverse direction between the proximal edges of the side seams. The remainder of the article except the elastic belt region 40 is considered the crotch region 30.

While not depicted, the wearable article 20 of the present invention may be the taped-type having a longitudinal centerline L1, a transverse centerline T1, a body facing surface, and a garment facing surface. The wearable article 20 may have a central chassis 38 comprising a front region 26, a back region 28, and a crotch region 33, each defined by a laterally extending line divided along the longitudinal axis in 3 equal lengths. The front region 26 and/or the back region 28 may be provided with fastening members for fastening the article to configure the waist opening and leg openings. The fastening member may be made by a connecting part connecting to the central chassis 38, a stretchable part which is stretchable in the lateral direction, and an engaging part having engaging elements such as hooks. The front region 26 and/or the back region 28 may be provided with a landing zone for receiving the engaging elements of the fastening member. The landing zone may be loops engageable with the hooks, or bonded nonwoven material, the nonwoven material including the subject nonwoven substrate of the present invention.

Figure 3:
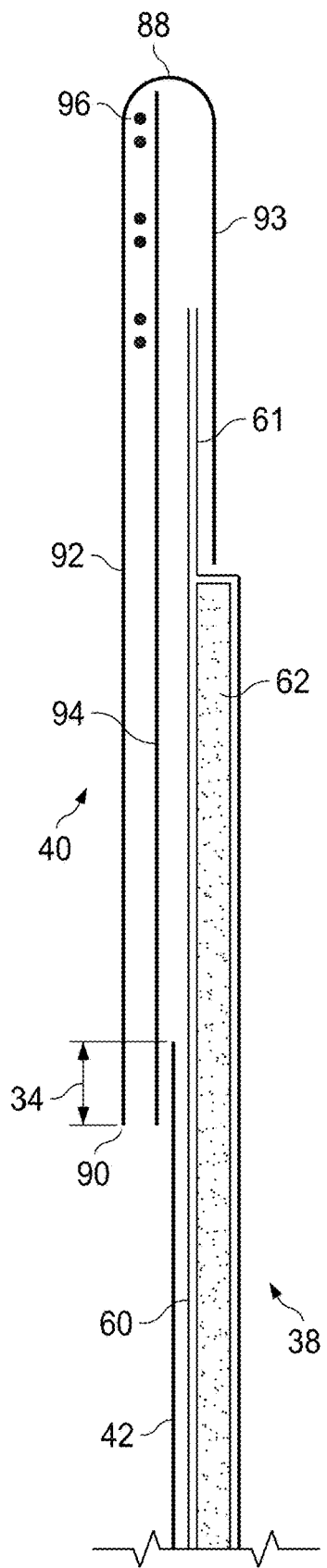
FIG. 3 is a cross section view of FIG. 2 taken along the longitudinal center line.

Referring to FIG. 3, the central chassis 38 comprises a backsheet 60 and an outer cover layer 42 for covering the garment-facing side of the backsheet 60. The backsheet 60 may be a water impermeable film. The outer cover layer 42 may be the nonwoven substrate of the present invention. The central chassis 38 may contain an absorbent core 62 for absorbing and containing body exudates disposed on the central chassis 38. In the embodiment shown in FIG. 2, the central chassis 38 has a generally rectangular shape, left and right longitudinally extending side edges 48 (hereinafter may be referred to as "side edge") and front and back transversely extending end edges 50 (hereinafter may be referred to as "end edge"). The central chassis 38 also has a front waist panel 52 positioned in the front region 26 of the wearable article 20, a back waist panel 54 positioned in the back region 28, and a crotch panel 56 between the front and back waist panels 52, 54 in the crotch region 30. The center of the front belt 84 is joined to a front waist panel 52 of the central chassis 38, the center of the back belt 86 is joined to a back waist panel 54 of the central chassis 38, the front and back belts 84, 86 each having a left side panel and a right side panel 82 where the central chassis 38 does not overlap.

The elastic belt region of the pant-type article of the present invention acts to dynamically create fitment forces and to distribute the forces dynamically generated during wear. The proximal edge 90 is located closer than the distal edge 88 relative to the crotch panel 56 of the central chassis 38. The front and back belts 84, 86 may be joined with each other only at the side edges 89 at the seams 32 to form a wearable article having a waist opening and two leg openings. Each leg opening may be provided with elasticity around the perimeter of the leg opening. For the belt-type pant, the elasticity around the leg opening may be provided by the combination of elasticity from the front belt 84, the back belt 86, and any from the central chassis 38.

The transverse width of the backsheet 60 and the outer cover layer 42 may be the same, or may be varied (not shown). For example, the backsheet 60 may have a shorter transverse width compared to that of the outer cover layer 42. By such configuration, the longitudinal side edges 48 of the crotch panel 56, which make part of the leg openings, may have better breathability. Further, such configuration may provide cost saving.

The front belt 84 and back belt 86 of the pant-type article are configured to impart elasticity to the belt 40. The front belt 84 and the back belt 86 may each be formed by a laminate comprising a plurality of elastic bodies 96 running in the transverse direction, an inner sheet 94, an outer sheet 92, and an outer sheet fold over 93 wherein the outer sheet fold over 93 is an extension of the outer sheet material formed by folding the outer sheet material at the distal edge 88 of the front and back belts; wherein the belt elastic bodies 96 are sandwiched between two of these sheets. The outer sheet 92 may be the nonwoven substrate of the present invention. The outer sheet 92 and the inner sheet 94 may be the nonwoven substrate of the present invention. The outer sheet 92 may be made of the same nonwoven substrate of the present invention as the outer cover layer 42 to provide integral aesthetic and tactile senses for the article.

The garment facing surface of the present article of either the taped-type or pant-type, as well as the elastic belt region 40 of the pant-type article; may be closely associated with the function and quality of the article, thus materials for forming these surfaces are carefully selected by the manufacturer for providing the desirables for the article. Soft, silky, cushiony, lofty touch of these surfaces, and undergarment kind of appearance of these surfaces may be associated with high quality, and thus generally favorably accepted by the user. The user may be the wearer or the caregiver. As such, use of materials which provide the aforementioned tactile and aesthetic sense is desired. However, it requires much resources to select the materials by having to create the finally assembled article for testing its performance by the user. It would be advantageous to have a method of selecting the material by use of a set of parameters measurable of the material per se, for predicting its tactile and aesthetic acceptance when assembled as an article.

The tactile and aesthetic acceptance of the nonwoven substrate of the present invention may be predicted by the "Fiber Surface Morphology Analysis" herein where the image of a SEM photo of the fiber of the subject nonwoven substrate is analyzed by the aid of image analysis software, as described in detail below. Referring to FIGS. 4A-4D, these are filtered SEM image photos taken by this process obtained by the nonwoven substrate of the present invention as well as other fibers. FIGS. 4A-4D are used for obtaining the fiber diameter, Roughness (standard deviation of the grayscale image) Skewness, and Kurtosis parameters, as described below. FIGS. 5A-5D are micro hole images extracted from the photos of FIGS. 4A-4D, according to the process, also described in detail below. FIGS. 5A-5D are used for obtaining the micro hole surface area (%), hole count/10 $\mu m^2$ (value), average hole size ($\mu m^2$), and total hole area/10 $\mu m$ ($\mu m^2$) parameters, as described below.

Figure 4A:
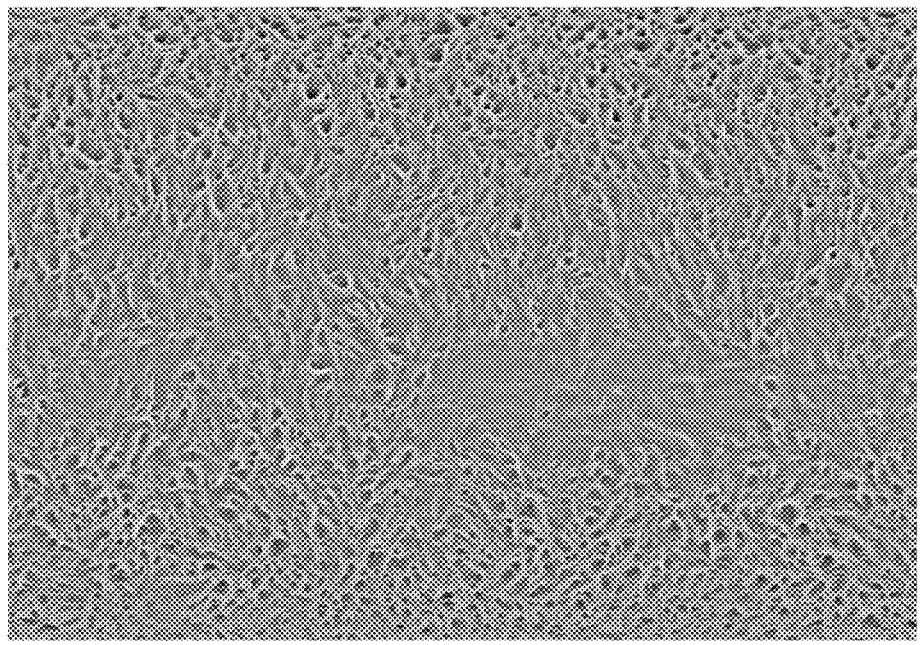
FIGS. 4A-4D are filtered SEM photos of fibers of the nonwoven substrates of the present invention and otherwise, according to the "Fiber Surface Morphology Analysis".
Figure 4B:
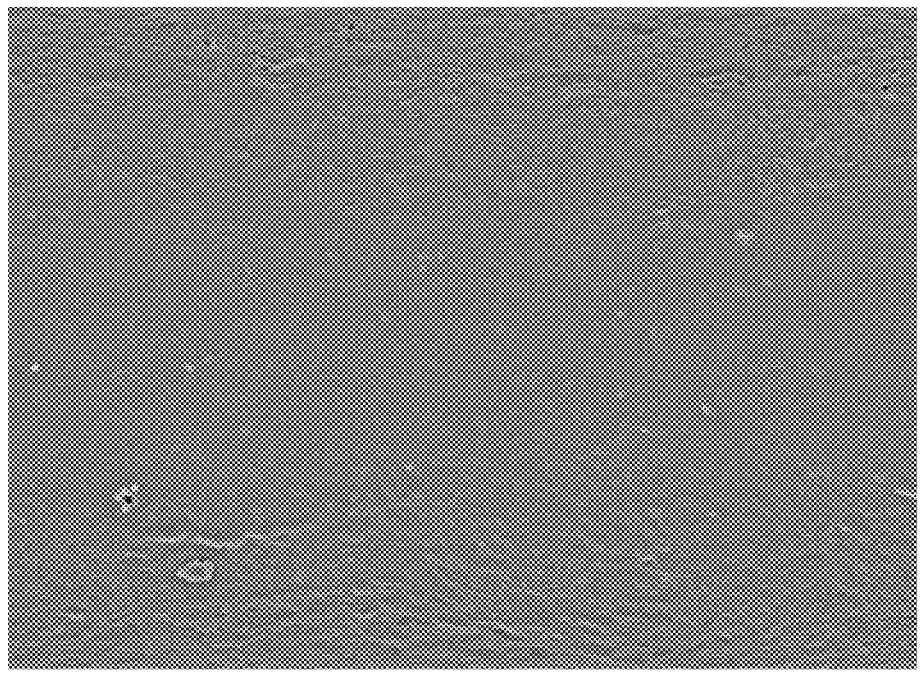
Figure 4C:
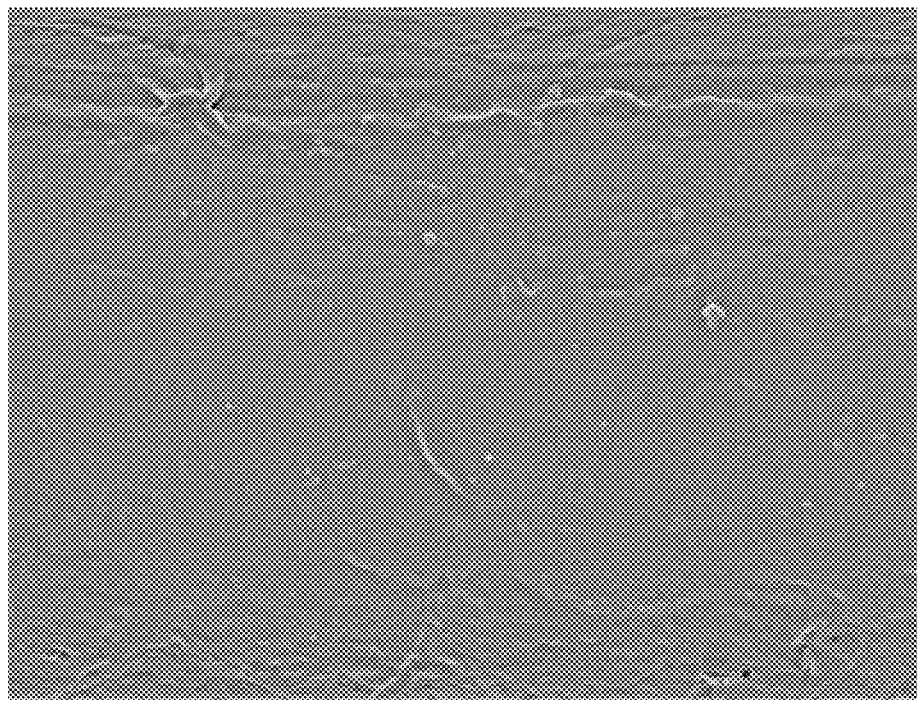
Figure 4D:
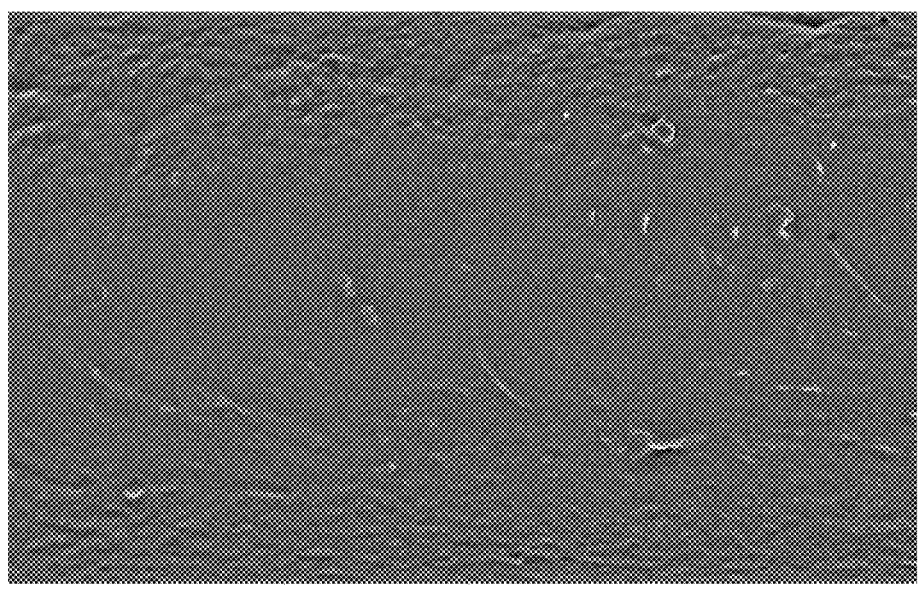

Referring to FIG. 4A and data points below, the nonwoven substrate of the present invention has a Roughness (standard deviation of the grayscale image) of at least about 16, or at least about 18, or at least about 20, and a fiber diameter of no more than about 22 $\mu m$, or no more than about 17 $\mu m$, or no more than about 15 $\mu m$, according to the measurements herein. Without being bound by theory, it is believed that nonwoven substrates having a fiber diameter that is less than a certain threshold, while having relatively higher Roughness (standard deviation of the grayscale image), provide favorable tactile sense to the skin. It is believed that when the fiber diameter of a nonwoven substrate is less than a certain threshold, the spacing between individual fibers, as well as the surface morphology of the fiber, are no longer perceivable by tactile sense. Meanwhile, the greater the Roughness (standard deviation of the grayscale image) of a fiber, the less contact of the fiber surface to the skin, thus there is less heat conductivity upon contact, such that a warm and soft tactile sense is perceived. Hence, without being bound by theory, the combination of relatively smaller fiber diameter and relatively higher Roughness (standard deviation of the grayscale image) provide the favorable soft tactile sense to the skin.

Figure 5A:
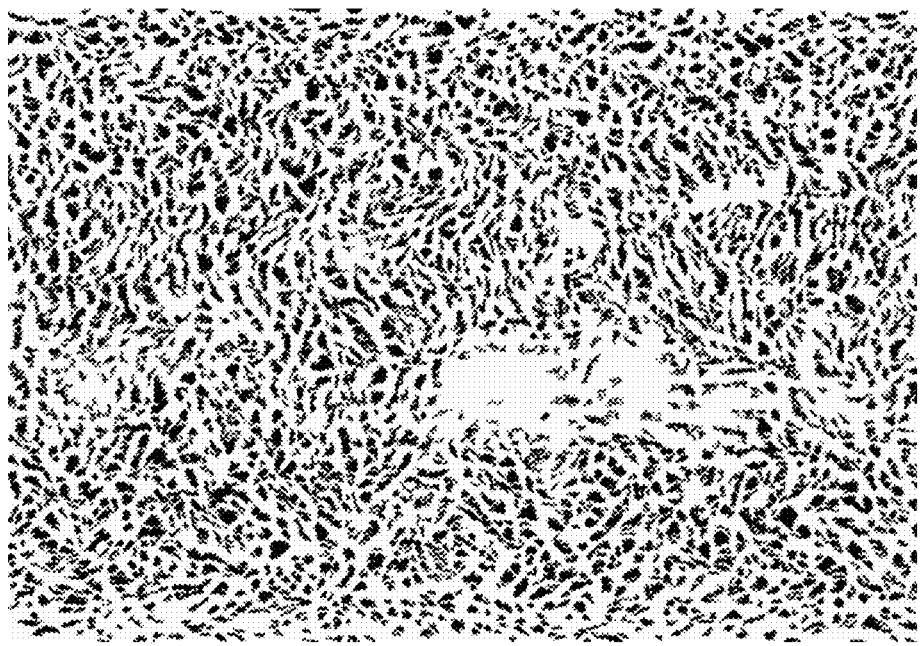
FIGS. 5A-5D are micro hole images extracted from the SEM photos of FIGS. 4A-4D according to the "Fiber Surface Morphology Analysis".
Figure 5B:
Figure 5C:
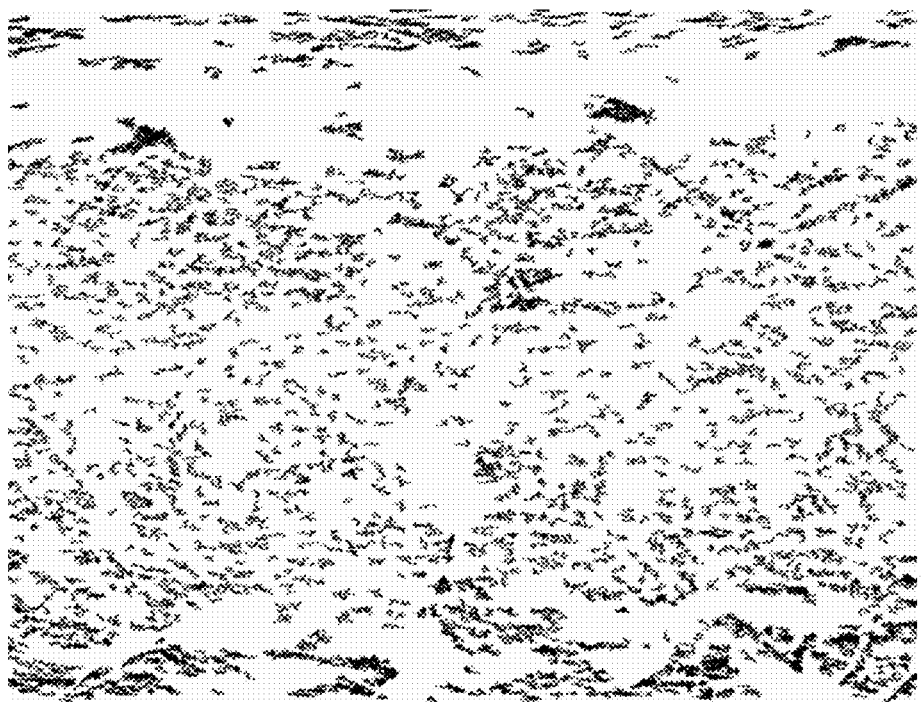
Figure 5D:
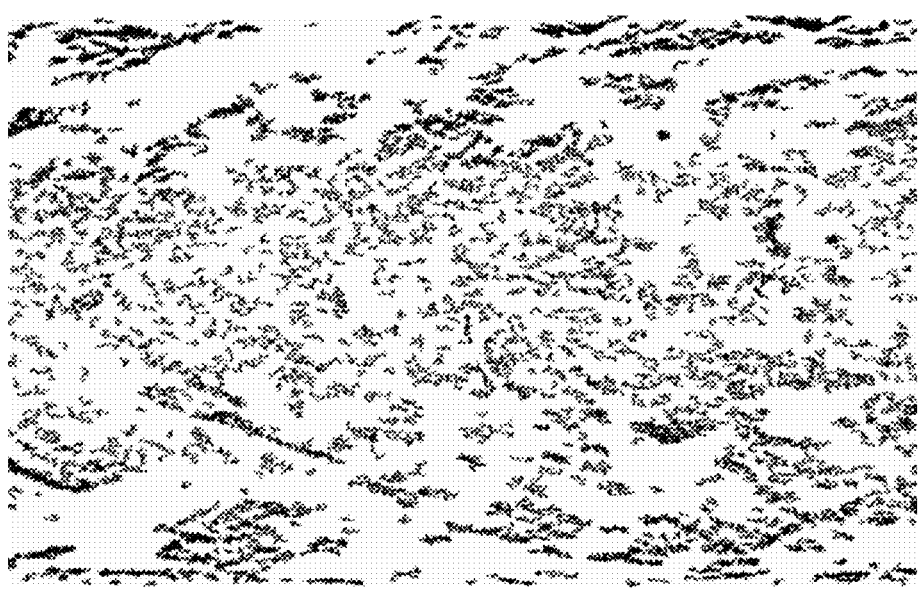

Referring to FIG. 5A and data points below, the nonwoven substrate of the present invention may have a micro hole surface area of at least about 20%, or at least about 22%, or at least about 24%, according to the measurements herein. The nonwoven substrate of the present invention may have a hole count/10 $\mu m^2$ of at least about 560, or at least about 575, or at least about 590, according to the measurements herein. The parameter of hole count/10 $\mu m^2$ is believed to be indicative of the roughness of the fiber surface. The nonwoven substrate of the present invention may have an average hole size of at least about 0.039 $\mu m^2$, or at least about 0.042 $\mu m^2$, according to the measurements herein. The parameter of average hole size is believed to be indicative of the degree of surface contact, wherein the greater the hole size, the less surface contact. The nonwoven substrate of the present invention may have a diameter of no more than about 17 $\mu m$, and a total hole area/10 $\mu m$ of at least about 27 $\mu m^2$, or at least about 29 $\mu m^2$, or at least about 33 $\mu m^2$, according to the measurements herein. The parameter of total hole area/10 $\mu m$ is believed to be indicative of the roughness of the fiber surface. In summary, without being bound by theory, it is believed that the greater the hole count/10 $\mu m^2$, the average hole size, or the total hole area/10 $\mu m$, the more softer the tactile sense to the skin.

Referring to FIG. 4A and data points below, the nonwoven substrate of the present invention may have a negative value in Skewness. The nonwoven substrate of the present invention may have a Kurtosis of less than about 3. Without being bound by theory, it is believed that such morphology characteristics further contribute to the soft and silky tactile sense to the skin.

Accordingly, by the "Fiber Surface Morphology Analysis" herein, one may predict if the nonwoven substrate material provides tactile and aesthetic acceptance to the user when assembled as an article. Referring to FIGS. 4B-4D and 5B-5D, and data points below, there exist nonwoven substrate material made of fibers which are similar in composition as that of the present invention, but exhibit different "Fiber Surface Morphology Analysis" characteristics as those of the present invention. The fibers of the nonwoven substrate of the present invention exhibit unexpectedly high roughness of fiber surface compared to fibers having similar fiber diameter. Without being bound by theory, these unique parameters of the nonwoven substrate of the present invention are believed to provide the improved soft, silky cushiony, and lofty tactile sense to the skin.

The nonwoven substrate of the present invention may have a certain material thickness to provide the lofty undergarment-like appearance and feel, for example, at least about 0.25 mm, or at least about 0.3 mm. The nonwoven substrate of the present invention may have a basis weight of at least about 17 gsm, or at least about 20 gsm. The basis weight and material thickness herein are related to materials obtained from a finished product according to the "Preparation for Thickness and Basis Weight" below and measured by "Base caliper method—ASTM D 654 Standard Test Method for Thickness of Paper and Paper Board" with modification of the loading to 500 Pa, and by "Basis weight—ASTM D 756 Practice for Determination of Weight and Shape Changes of Plastics Under Accelerated Service Conditions", respectively. Suitable for the nonwoven substrate of the present invention are air-through carded nonwoven material made of co-centric bicomponent fiber, crimping fiber made through core eccentric bicomponent filament or side by side bicomponent filament. Non-limiting examples of materials suitable for nonwoven substrate of the present invention include: 20-50 gsm air-through carded nonwoven substrate made of less than 15 μm diameter PE/PET bi-component staple fiber, such as those with a tradename of FJ206 available from Dayuan, Beijing China.

Referring to FIG. 2, a belt-type pant article embodiment of the present invention is described in further detail. The front belt 84 and the back belt 86 may each be made only by elastic bodies 96, the inner sheet 94, the outer sheet 92, and the outer sheet fold over 93. The belt elastic bodies 96 may extend in the transverse direction to provide a ring like elastic belt 40 when the front belt 84 and the back belt 86 are joined. At least some of the elastic bodies 96 extend in the transverse direction substantially parallel to each other. All of the elastic bodies 96 may extend in the transverse direction substantially parallel to each other. Such an article may be economically made. The front and back belt 84, 86 each may have transversely continuous proximal and distal edges, the proximal edge 90 being located closer than the distal edge 88 relative to the longitudinal center of the article. The elastic bodies 96 may be disposed in the same or different denier, interval, and force between the front and back, as well as in different longitudinal positions of the belt.

The front and/or back belt 84, 86 may be treated such that certain of the area overlapping the front and/or back waist panel 52, 54 of the central chassis 38 are removed of elasticity. Removal of elasticity from a certain area of the front and/or back waist panel 52, 54 may be advantageous when the central chassis 38 comprises an absorbent core 62, in that elasticity in the front and/or back area overlapping the absorbent core 62 may cause bunching of the absorbent layer or any of the layers in the absorbent core 62 and interfere with close fit of the central chassis 38 to the wearer.

In one embodiment, at least a portion of, or at least 10% of, or at least 20% of, or at least 30% of, the elasticity of; at least one of, or at least half of, or at least two thirds of, the elastic bodies are removed in the region overlapping with the front and back waist panels 52, 54 of the central chassis 38. Referring to FIG. 2, the entire area where the elastic bodies 96 overlap with the absorbent core 62 may be removed of its elasticity as in the front belt 84. Alternatively, as seen in the back belt 86, the elastic bodies 96 overlapping the absorbent material non-existing region 61 and toward the distal edges of the absorbent core 62 may be disposed in active elasticity for good fit of the central chassis 38. This may be advantageous in preventing leakage.

Referring to FIG. 2, the transverse width LW of the back belt 86 in the uncontracted condition may be the same as the transverse width of the front belt 84 of the same condition. Such an article may be economically made.

The longitudinal length LB of the back belt 86 between the back distal edge 88 and the back proximal edge 90 along its entire width LW of the back belt 86 may be approximately the same as the longitudinal length LF of the front belt 84 between the front distal edge 88 and the front proximal edge 90. In such configuration, the seams 32 close the front and back belt 84, 86 side edges 89 of the same length for forming the article. Such an article may be economically made.

The back belt 86 may have a greater longitudinal length LB between the back distal edge 88 and the back proximal edge 90 along its entire width LW of the back belt 86 in the transverse direction than the longitudinal length LF of the front belt 84 between the front distal edge 88 and the front proximal edge 90 (FIGS. 1 and 2). In such configuration, when the wearable article is assembled to form the waist opening and the leg openings, the wearable article 20 is folded along the transverse centerline T1 such that the front distal edge 88 is aligned with the back distal edge 88. The front side edge 89 is also aligned with a portion of the back side edge 89. Then the front belt 84 and the back belt 86 are joined at the front and back side edges 89 at the seams 32. The front and back proximal edges 90, however, may not be aligned to one another. The back proximal edge 90 may be disposed longitudinally closer than the front proximal edge 90 relative to the transverse center line T1 such that the proximal portion of the back side panel 82 extends toward the crotch panel 56 of the central chassis 38 beyond the front proximal edge 90. The side edge of the proximal portion of the back side panel 82 may not be joined to anywhere and free from attachment. Thus, the proximal portion of the back side panel 82 provides a buttock cover 95 as in FIG. 1.

The article of the present invention may have a suitable Stretch Circumference Force (N). What is meant by Stretch Circumference Force is the loading force at a certain stretch level which is believed to simulate initial stretch experience felt by the user when inserting hands and stretch opening the article. The level of stretch which is believed to be felt by the user when stretch opening the article is represented by the "470 mm Stretch Circumference". The dimension of 470 mm is selected based on a study by the Applicant whereby the average standing hip circumference (mm) at the height matching the pubic bone of children having a body weight of 6-20 kg was 473 mm based on data from over 1000 subjects. Namely, according to common habits for wearing a pant article, the user would stretch open the elastic belt region of the pant article to a circumference more or less matching that of the hip circumference of the body of the wearer. A body weight of 6-20 kg matches the recommended body weight of wearers for pant articles of Sizes 3-6 (Sizes M to XXL). The article of the present invention has a Stretch Circumference Force of no greater than about 7N, or no greater than about 6.5N, or no greater than about 6N. By having such Stretch Circumference Force, the elastic belt can be easily opened and applied. Without being bound by theory, it is believed that the lower the Stretch Circumference Force, the elastic belt region may be stretched with less force, thus softer the perception of the elastic belt region by the user.

The article of the present invention may have a suitable Fit Circumference Force (N). What is meant by Fit Circumference Force is the unloading force at a certain stretch level which is believed to simulate the force felt by the wearer while wearing the article. The level of stretch which is believed to be felt by the wearer while wearing the article is also represented by the 470 mm Stretch Circumference. The article of the present invention has a Fit Circumference Force of no less than about 2N. By having such Fit Circumference Force, the elastic belt provides good fit to prevent sagging and leakage.

Without being bound by theory, it is believed that by having a relatively low Stretch Circumference Force of no greater than about 7N in combination with a Fit Circumference Force of no less than about 2N, an elastic belt region having ease of application and a secure yet soft fit may be provided. Without being bound by theory, it is believed that by providing the aforementioned Stretch Circumference Force and Fit Circumference Force, the pant-type article of the present invention provides an overall satisfactory tactile sense to the user upon touching, applying, and wearing the article.

Referring to FIG. 3, for the belt-type pant the front and back belts 84, 86 are discontinuous with one another in the crotch region 30, and the outer cover layer 42 is the garment-facing surface in the crotch region 30. The outer cover layer 42 may extend only partly in the longitudinal direction of the front waist panel 52 and the back waist panel 54 to leave the distal parts of the front waist panel 52 and the back waist panel 54 free of the outer cover layer 42. Namely, the longitudinal length of the outer cover layer 42 may be longer than the longitudinal length of the crotch panel 56 and shorter than the longitudinal length of the backsheet 60. By such configuration, the distal parts of the front waist panel 52 and the back waist panel 54 are devoid of the outer cover layer 42, providing better breathability to the overall article. Further, this may provide cost saving of the outer cover layer 42 material. Accordingly, looking at the layers of elements between the garment facing surface and the backsheet of the center chassis 38 of FIG. 3, there exists a transitional region 34 disposed on the waist panel 52 where the outer cover layer 42 is present. The longitudinal length of the transitional region 34 may be made as short as possible, for example, less than about 20 mm, or less than about 15 mm, or less than about 10 mm. Further, adhesive may be applied on the entire area of the transitional region 34, or the entire area leaving no more than up to 5 mm, in the longitudinal direction, from the distal edge of the transitional region 34. For providing attractive artwork for a wearable article in an economical manner, printing may be provided on the garment facing side of the backsheet 60. By providing the transitional region 34 as short as possible, applying adhesive to the transitional region 34 to enhance transparency, or simply avoiding displaying artwork in the transitional region 34, compromised appearance of the artwork over different layers of material between the artwork and the observer may be avoided.

Alternatively, when artwork provided on the backsheet 60 extends across the elastic belt region 40 and the crotch region 30, the area of the artwork in the belt region 40 may be provided in reduced brightness and increased contrast compared to the area in the crotch region 30; such that the intensity of the artwork appear to be substantially similar when observed as an article from the garment facing side. By providing the artwork in reduced brightness and increased contrast, the artwork is less influenced by opaqueness provided by the overlaying layers of material.

Alternatively and/or additionally, the artwork in the elastic belt region 40 may be printed on the garment facing surface of the inner sheet 94 or the body facing surface of the outer sheet 92, and the artwork in the crotch region 30 may be printed on the backsheet 60. By printing the artwork in these specific layers, the number of layers between the garment facing surface and the printing may be made equal, thus the appearance difference may be alleviated. The opacity difference between the outer sheet 92 and the outer cover layer 42 may be minimized by selecting the layers to match the opacity, or by disposing the same material. The artwork for the elastic belt region 40 may be printed directly on the inner sheet 94 or the outer sheet 92 by ink, or by disposing a colored web of a predetermined shape.

As mentioned above, the front belt may have a longitudinal length of LF; and the back belt may have a longitudinal length of LB, and the outer sheet fold over 93 is formed by folding the outer sheet material at the distal edge 88 of the front and back belts. The front outer sheet fold over 93 may have a longitudinal length of at least about 0.3LF, or from about 0.3LF to about 0.7LF, or from about 0.5LF to about 0.7LF. The back outer sheet fold over may have a longitudinal length to match the length of the front outer sheet fold over. Namely, the back outer sheet fold over may have about the same length as the front outer sheet fold over.

As mentioned above, the elastic belt region 40 exhibits elasticity due to the plurality of elastic bodies 96 running in the transverse direction, wherein the elastic bodies 96 are adhered to the inner and outer sheets 92, 94. Tensile stress of the elastic belt region 40 may be adjusted by one or more of the following methods; 1) elongation rate of the elastic body 96; 2) density (dtex) of the elastic body 96; 3) longitudinal interval of multiple elastic bodies 96; and 4) effective length of elasticity of the elastic body 96 in the transverse direction. The elastic bodies may be elastic strands having a dtex of from about 470 to about 1100 and disposed at an elongation of from about 110% to about 290%. By elongation, "0% elongation" is meant the original length of the elastic body 96. Some elastics may be disposed to impart higher tensile stress in certain regions. Such one or more elastics of higher tensile stress may be disposed in an array of 2-4 elastic strands having an interval within the array of between 2-4 mm. The array may be disposed on the front belt between the longitudinal length of from about 0.5LF to about 0.85LF from the waist opening. The array may be disposed on the back belt between the longitudinal length of from about 0.25LF to about 0.5LF from the waist opening.

The pant-type articles of the present invention provide overall softness and the perception of being easy to apply, comfortable for the wearer to wear, allowing the wearer to move at ease, undergarment like, and overall high quality.

1. Fiber Surface Morphology Analysis 1-1. Sample Preparation

The surface morphology of fibers in a sample of a nonwoven substrate material is determined by using a Scanning Electron Microscope (SEM) such as Hitachi Model S-4800 or equivalent equipment. The material is sampled from the garment-facing surface of absorbent articles, from a part where there is little adhesive, by gently peeling off from other layers and cutting it into a suitable size of 5 mm×5 mm. The samples are mounted on a sample stage with carbon tape. Then the samples are sputtered with platinum to avoid electric charging and improve overall conductivity under the conditions of 15 mA current and 120 s coating time. The platinum-coated samples are subsequently transferred into the SEM sample chamber. After this, the chamber pressure is controlled below $1\times10^{-3}$ Pa.

1-2. Instrument Preparation

Turn on the accelerated voltage of 3 kV. A magnification of 5,000 times and working distance of about 8 mm are chosen such that the fibers are suitably enlarged for measurement. The fiber length direction is substantially aligned to the horizontal direction and positioned at substantially center of the vertical direction of the imaging display. Total 5 fibers are randomly selected across the sample of the nonwoven substrate material and imaged using the SEM with 8 bits jpeg image at resolution 960 pixels (height)× 1280 (width).

1-3. Surface Morphology and Fiber Diameter Analysis

Fiber diameter, Roughness (standard deviation of the grayscale image), Skewness, Kurtosis, micro hole surface area (%), hole count/10 $\mu m^2$ (value), average hole size ($\mu m^2$), and total hole area/10 $\mu m$ ($\mu m^2$) are obtained by analyzing SEM image with ImageJ software (1.48v or later version) developed by Wayne Rasband of National Institutes of Health, USA or equivalent software. FIGS. 4A-4D are filtered SEM image photos taken by this process for various nonwoven fibers.

Next, the measurement scale should be set referring to the SEM scale bar. Then, the fiber diameter is measured by using line tool. For the surface morphology analysis, the SEM image is cropped to the rectangle shape that captures only fiber part with almost full width of the fiber but avoiding light reflection parts at the fiber edges. The length of the fiber in the cropped rectangle shape should have a length of at least 20 $\mu m$. The surface morphology information includes the base cylindrical shape of the fiber. The base cylindrical shape is removed by using FFT Bandpass filter set at range 0-20 pixels and auto scaling. The contrast and brightness is adjusted for capturing as much surface morphology as possible. FIGS. 5A-5D are micro hole images extracted from the photos of FIGS. 4A-4D, according to this process. Roughness (standard deviation of the grayscale image), Skewness, Kurtosis, Area $\mu m^2$ (image area) and Width $\mu m$ (image width) are obtained by using standard measurement function. Area $\mu m^2$ is used for the later analysis. The threshold is set at closest 35% percentile from lower side for further analysis. The values of count, total area, average size and % area are obtained by using "Analyze Particles" tool set at "Size" 0.01-Infinity and "Circularity" 0.05-1.00. Micro hole surface area (%), hole count/10 $\mu m^2$ (value), average hole size ($\mu m^2$), and total hole area/10 $\mu m$ ($\mu m^2$) are defined as follows.

Micro Hole Surface area=% Area (No calculation)

Hole count/10 $\mu m^2$=Count/Area ($\mu m^2$×100

Average hole size=Average size ($\mu m^2$)

Total hole area $\mu m^2$/10 $\mu m$=Total Area/Width (image width)×10

Each test sample is analyzed across 5 SEM fiber images following the description above. The mean value of each measurement is obtained to define representative measurement value of the test sample.

2. Preparation for Thickness and Basis Weight

The following sampling procedures are taken for measuring thickness and basis weight of a material used in a finished article.

To obtain a sample from a finished article, when available, an area free of deformation or wrinking is selected. For the inner sheet 94 or outer sheet 92 of a pant-type article, when available, area where the elasticity is deactivated is selected. The outer sheet 92, inner sheet 94, or outer cover layer 42 is separated from the other components such as belt laminated nonwoven layers, or backsheet film by techniques such as applying "Quik-Freeze®" type cold spray, or other suitable methods that do not permanently alter the properties of the nonwoven composition. The technical face-side is the surface intended to be used as the garment-facing surface for the outer sheet 92 or outer cover layer 42, and the body-facing surface for the inner sheet 94. Care should be taken to prevent stretching of the nonwoven composition during the separation process. A 100 mm by 100 mm square shape is cut out using a cutter and a 100 $cm^2$ die for obtaining the sample.

For measuring the basis weight, any remaining adhesive is removed from the sample by the following steps using Tetrahydrofuran (THF) as solvent.

1. In a Hood, Transfer 1 Liter of THF into the 3-4 Liter Beaker
2. Submerge sample in the 1 liter of THF
3. Place beaker on shaking table and stir gently for 15 minutes and keep solution with sample sit for 5 additional minutes
4. Take sample out of THF solution, and carefully squeeze THF solution out of sample.
5. Let sample air dry in hood for a minimum of 15 minutes Samples are obtained from ten (10) finished articles and cut out from the same area of each article, for each set of measurement. Samples are pre-conditioned in a room maintained at 23±2° C. and 50±5% relative humidity, for at least 2 hours prior to testing.

3. Whole Article Force Measurement

Force of a pant-type article is measured using an Electronic Tensile Tester with a computer interface such as the MTS Criterion C42 running TestWorks 4 Software (available from MTS SYSTEMS (CHINA) CO., LTD) or equivalent instrument. A load cell is selected so that force results for the samples tested will be between 10 and 90% of capacity of the load cell used. The instrument is calibrated according to the manufacturer's instructions. All testing is performed in a room maintained at 23±2° C. and 50±5% relative humidity.

Figure 6:
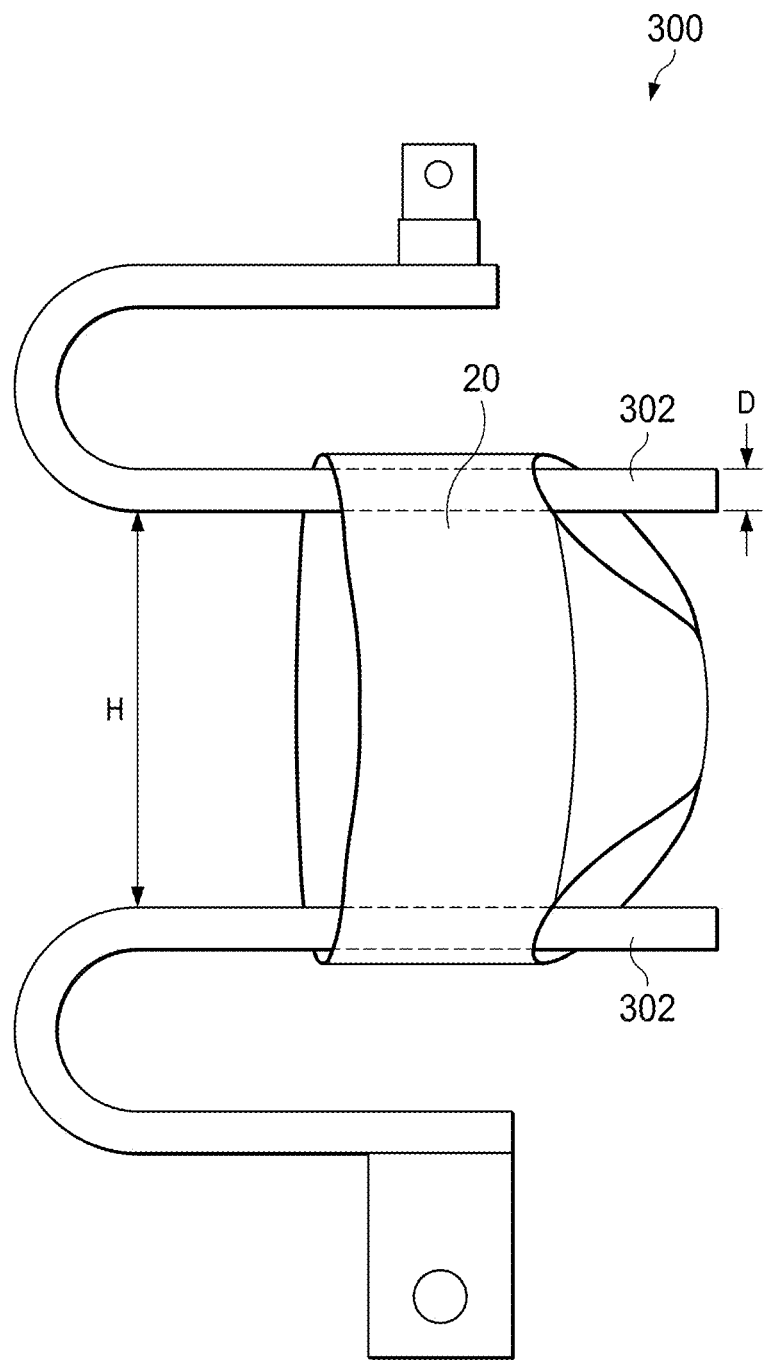
FIG. 6 is a schematic view of an example of a hanger-type sample holding fixture according to the "Whole Article Force Measurement".

The tensile tester is fitted with hanger-type sample holding fixtures 300 as shown in FIG. 6. Each fixture comprises a rigid linear rubber-coated horizontal bar section 302 to prevent sample slippage during testing. The outer bar diameter (including the rubber coating) of the horizontal bar sections is 10.0 mm. The central axes of the horizontal bar sections 302 are configured to remain parallel and in the same vertical plane throughout the test procedure. The gauge circumference is determined by the following equation:

Gauge Circumference=2×(H+D+πD/2)

where H is the vertical gap between the horizontal bar sections 302, and D is the outer diameter of the bar.

The instrument is set up to go through the following steps:

| | |
|---|---|
| Crosshead Speed | 254.0 mm/min |
| Final Load Point | 19.6 N |
| Hold Time | 0 |
| Number of Cycles | 1 |
| Data Acquisition Rate | 50 Hz |

A sample article 20 is inserted onto the upper horizontal bar section 302 so that the bar passes through the waist opening and one leg opening of the article. The crosshead is raised until the specimen hangs above the lower bar and does not touch lower bar 302. The load cell is tared and the crosshead is lowered to enable the lower bar 302 to be inserted through the waist opening and other leg opening without stretching the article. The article is adjusted so that the longitudinal centerline L1 of the article is in a horizontal plane halfway between the upper and lower bars 302. The center of the side portion in contact with the bar 302 is situated on the same vertical axis as the instrument load cell. The crosshead is raised slowly while the article is held in place by hand as necessary until the force is between 0.05 and 0.1N, while taking care not to add any unnecessary force. The gauge circumference at this point is the Initial Gauge Circumference. The test is initiated and the crosshead moves up at 254 mm/min until a force of 19.6N is attained, then the crosshead immediately returns to the Initial Gauge Circumference at the same speed. The maximum circumference at 19.6N during the extension segment of the test is recorded.

The maximum circumference at 19.6N is defined as the Full Circumference (mm). The force at a circumference of 470 mm is defined as the 470 mm Stretch Circumference (mm). The Stretch Circumference Force is defined as the force at 470 mm Stretch Circumference during the load (extension) segment of the test. The Fit Circumference Force is defined as the force at 470 mm Stretch Circumference during the unload (contraction) segment of the test.

Five samples are analyzed and their average Initial Gauge Circumference, average Full Circumference, average Stretch Circumference Force and average Fit Circumference Force are calculated and reported to the nearest 1 mm or 0.01 N, respectively.

EXAMPLES

Examples 1 and A-C having the structure of a pant type wearable article are obtained as such, and some were subject to measurements as described above, and consumer acceptance tests described below.

Example 1

Size 4 belt-type pant articles having the configuration of FIG. 2 and elastic profiles of Table 1 below, with the outer sheet and outer cover layer made by tradename FJ206 available from Dayuan, Beijing China (20 gsm air-through carded nonwoven substrate with 15 μm diameter PE/PET bicomponent fiber) and the inner sheet made by tradename HY15015-MALAYSIA-V2 available from Fibertex (15 gsm PP spunbond nonwoven substrate).

Example A

A Size 4 belt-type pant article sold by the tradename of "Anerles Gold Pants" purchased in the Peoples Republic of China during October to November 2015.

Example B

A Size 4 belt-type pant article Size 4 uni-body type pant article sold by the tradename of "GooN Premium Pants" purchased in the Peoples Republic of China during October to December 2016 having Lot #20160614CA114400519, 27.

Example C

A Size 4 uni-body type pant article sold by the tradename of "Merries Pants" purchased in the Peoples Republic of China during October to November 2015 having Lot #20150124EOC30245.

TABLE 1

| | dtex/elongation %/ number of elastic bodies |
|---|---|
| Front 0-25% LF from waist opening | 540dtex/150%/4 |
| Front 25-50% LF from waist opening | 540dtex/150%/2 |
| | 540dtex/150%/2 tummy cut (*1) |
| Front 50-85% LF from waist opening | 940dtex/210%/8 tummy cut (*1) |
| Front 85-100% LF from waist opening | 540dtex/150%/2 tummy cut (*1) |
| Back 0-25% LF from waist opening | 540dtex/150%/4 |
| Back 25-50% LF from waist opening | 940dtex/130%/4 |
| Back 50-85% LF from waist opening | 540dtex/210%/2 |
| | 540dtex/210%/4 tummy cut (*1) |
| Back 85-100% LF from waist opening | 540dtex/210%/2 tummy cut (*1) |

(*1) tummy cut in Table 1 refers to removal of elasticity at the central area of elastic strands which overlap the central chassis 38, resulting in 66% effective length of elasticity.

The outer cover layers of Examples 1 and A-C were subject to the Fiber Surface Morphology Analysis described above, and provided results as in Tables 2 and 3 below.

TABLE 2

| Example | FIG. | Fiber diameter (μm) | Roughness | Skewness | Kurtosis |
|---|---|---|---|---|---|
| 1 | 4A | 13.9 | 22.6 (*2) | −0.1 (*2) | 1.1 (*2) |
| A | 4B | 14.6 | 12.6 | 0.4 | 4.9 |
| B | 4C | 15.6 | 12.5 | 0.5 | 4.6 |
| C | 4D | 13.5 | 11.3 | 0.7 | 6.0 |

TABLE 3

| Example | FIG. | micro hole surface area (%) | hole count/ 10 μm$^2$ | average hole size (μm$^2$) | total hole area/ 10 μm (μm$^2$) |
|---|---|---|---|---|---|
| 1 | 5A | 28 (*2) | 631 (*2) | 0.044 (*2) | 37 (*2) |
| A | 5B | 17 | 489 | 0.035 | 24 |
| B | 5C | 15 | 480 | 0.031 | 22 |
| C | 5D | 17 | 506 | 0.034 | 22 |

(*2) statistically significantly different than the remainder examples at 10% risk The articles of Examples 1 and A-C were subject to the Whole Article Force Measurement described above, and provided results as in Table 4 below.

TABLE 4

| Example | Full circumference (mm) | Stretch circumference force (N) | Fit circumference force (N) |
|---|---|---|---|
| 1 | 663 | 6.4 | 2.8 |
| A | 636 | 7.5 | 3.9 |

TABLE 4-continued

| Example | Full circumference (mm) | Stretch circumference force (N) | Fit circumference force (N) |
|---|---|---|---|
| B | 644 | 8.0 | 4.6 |
| C | 661 | 7.3 | 3.8 |

Consumer Acceptance Test 30 panelists who were caregivers of babies using Size 4 pants diapers at a frequency of minimum 3 pads per day, and having a mixture of usage experience of major brands: "Merries", "Huggies Gold" and "Pampers"; were recruited. Each panelist was given 9 test products altogether on a table. Among the 9 test products, Examples 1, A, and C were included. Example B was not included. The panelists were asked to sort the 9 products on to the scale 1-10 on the table for each question. The rating score of 30 panelists were averaged for the report as in Table 5. (The remainder of the 9 products except Examples 1, A, and C were; another prototype similar to Example 1 except for using a non-inventive nonwoven material for the garment facing side, "Huggies Gold Pants", "Huggies Silver Pants", "Mammy Poko Pants", "Anerle Silver Pants", and "Goon Pants", all purchased in the Peoples Republic of China during October to November 2015.)

TABLE 5

| Values/Questions | 1 | A | C |
|---|---|---|---|
| Overall liking | 8.3 | 7.4 | 8.4 |
| Being soft | 8.9 | 7.6 | 8.0 |
| Underwear like | 8.4 | 7.5 | 7.9 |

Inventive Example 1 which meets the parametric requirements of the present invention have high acceptance for "overall liking" and highest acceptance of "being soft" and "underwear like" while the other examples which do not meet the parametric requirements of the present invention are slightly to significantly inferior in consumer acceptance in at least some aspect. The parameters of the present invention provide a good predictability of consumer acceptance in view of tactile and aesthetic sense provided by the article.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Further, every numerical range given throughout this specification includes every narrower numerical range that falls within such broader numerical range.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A pant article continuous in a longitudinal direction and a transverse direction, comprising:
   a body-facing surface and a garment-facing surface;
   wherein at least a portion of the garment-facing surface is a nonwoven substrate made of fibers having a Roughness (standard deviation of the grayscale image) of at least 16; and a fiber diameter of no more than 22 µm;
   an elastic belt region, a crotch region, a waist opening, and two leg openings;
   wherein the elastic belt region is a laminate comprising an inner sheet, an outer sheet, and a plurality of elastic bodies configured to stretch the elastic belt region in the transverse direction;
   wherein the crotch region has an outer cover layer as the garment-facing surface; and
   wherein at least one of the inner sheet, the outer sheet, and the outer cover layer is the nonwoven substrate.

2. The pant article of claim 1 wherein the fiber of the nonwoven substrate has a micro hole surface area of at least 20%.

3. The pant article of claim 1 wherein the fiber of the nonwoven substrate has a hole count/10 µm$^2$ of at least 560.

4. The pant article of claim 1 wherein the fiber of the nonwoven substrate has an average hole size of at least 0.039 µm$^2$.

5. The pant article of claim 1 wherein the fiber of the nonwoven substrate has a diameter of no more than 17 µm.

6. The pant article of claim 1 wherein the nonwoven substrate has a basis weight of at least 17 gsm according to the measurements herein.

7. The pant article of claim 1 wherein the nonwoven substrate is an air-through carded nonwoven made of a bicomponent filament.

8. The pant article of claim 1 wherein the article comprises a central chassis and a ring-like elastic belt comprising a front belt and a back belt; the center of the front belt is joined to a front waist panel of the central chassis, the center of the back belt is joined to a back waist panel of the central chassis, and the remainder of the central chassis forms the crotch region, the front and back belt each having a left side panel and a right side panel where the central chassis does not overlap, and the transverse edges of the front belt and the back belt are joined by a seam to form a waist opening and two leg openings; wherein the front belt and the back belt are discontinuous of each other in the longitudinal direction.

9. The pant article of claim 1 wherein the outer cover layer is the nonwoven substrate.

10. The pant article of claim 1 wherein the outer sheet of the elastic belt region is the nonwoven substrate.

11. The pant article of claim 1 wherein the inner sheet of the elastic belt region is the nonwoven substrate.

12. The pant article of claim 1 having a Stretch Circumference Force of less than 7N according to the measurements herein.

13. The pant article of claim 1 having a Fit Circumference Force of at least 2N according to the measurements herein.

* * * * *